(12) United States Patent
Kaplit

(10) Patent No.: US 7,634,378 B2
(45) Date of Patent: Dec. 15, 2009

(54) DETECTION OF INSUFFICIENT SAMPLE DURING ASPIRATION WITH A PIPETTE

(75) Inventor: Michael Kaplit, Wilmington, DE (US)

(73) Assignee: Siemens Healthcare Diagnostics Inc., Deerfield, IL (US)

(*) Notice: Subject to any disclaimer, the term of this patent is extended or adjusted under 35 U.S.C. 154(b) by 35 days.

(21) Appl. No.: 11/948,065

(22) Filed: Nov. 30, 2007

(65) Prior Publication Data

US 2009/0144016 A1 Jun. 4, 2009

(51) Int. Cl.
*G06F 19/00* (2006.01)
(52) U.S. Cl. .......................... 702/140; 702/32; 702/55; 702/114; 340/605; 73/37; 73/1.36; 73/864.34; 73/149; 73/1.16
(58) Field of Classification Search .................. 702/140, 702/32, 55, 114; 73/1.16, 1.36, 37, 864.34; 73/149; 422/64; 340/615
See application file for complete search history.

(56) References Cited

U.S. PATENT DOCUMENTS

| 4,794,085 A | 12/1988 | Jessop et al. |
| 4,893,515 A | 1/1990 | Uchida |
| 5,400,664 A | 3/1995 | Kio |
| 5,463,895 A | 11/1995 | Brentz |
| 5,488,854 A | 2/1996 | Kawanabe et al. |
| 5,488,874 A * | 2/1996 | Kawanabe et al. ....... 73/863.01 |
| 5,503,036 A | 4/1996 | Nguyen et al. |
| 5,540,081 A | 7/1996 | Takeda et al. |
| 5,568,404 A | 10/1996 | Sturmolo |
| 5,723,795 A | 3/1998 | Merriam |
| 5,750,881 A | 5/1998 | Dorenkott et al. |
| 5,777,221 A * | 7/1998 | Murthy et al. ................. 73/149 |
| 5,915,282 A | 6/1999 | Merriam et al. |
| 5,964,381 A * | 10/1999 | El-Hage et al. ............. 222/386 |
| 5,965,828 A | 10/1999 | Merriam |
| 6,022,747 A * | 2/2000 | Gherson et al. ............... 436/69 |
| 6,060,320 A * | 5/2000 | Dorenkott et al. ............. 436/54 |
| 6,094,966 A | 8/2000 | Papen et al. |
| 6,119,533 A * | 9/2000 | Gherson et al. .......... 73/864.34 |
| 6,121,049 A * | 9/2000 | Dorenkott et al. ............. 436/50 |
| 6,250,130 B1 * | 6/2001 | Howard et al. ................ 73/1.36 |
| 6,370,942 B1 * | 4/2002 | Dunfee et al. .................. 73/37 |
| 6,456,944 B1 | 9/2002 | Burkhardt et al. |
| 6,938,504 B2 | 9/2005 | Camenisch |
| 7,097,623 B2 | 8/2006 | Colin et al. |
| 7,231,805 B2 | 6/2007 | Bretmersky |
| 7,477,997 B2 * | 1/2009 | Kaplit ......................... 702/55 |
| 2007/0025882 A1 | 2/2007 | Zuppiger et al. |
| 2007/0143063 A1 * | 6/2007 | Kaplit ........................ 702/140 |

* cited by examiner

*Primary Examiner*—Carol S Tsai
(74) *Attorney, Agent, or Firm*—Leland K. Jordan

(57) ABSTRACT

Analyzing the pressure profile generated during a limited period of time immediately prior to the end of a liquid aspiration process and comparing the standard deviation of the residuals to a critical value to determine if the liquid was of a desired sufficient volume.

8 Claims, 5 Drawing Sheets

US 7,634,378 B2

DETECTION OF INSUFFICIENT SAMPLE DURING ASPIRATION WITH A PIPETTE

FIELD OF THE INVENTION

The present invention relates to the aspiration of an amount of liquid from a container, and more particularly, to an improved method for ascertaining insufficient of sample volume during a liquid aspiration process.

BACKGROUND OF THE INVENTION

Fully automated diagnostic analyzers are commercially available to perform chemical assays and immunoassays of biological fluids such as urine, blood serum, plasma, cerebrospinal liquids and the like. Generally, reactions between an analyte in a patient sample and reagents used during the assay generate a signal from which the concentration of analyte in the patient sample may be calculated. Such automated analyzers generally use an aspirating means such as a sampling tip, or probe or needle, to transfer desired volumes of liquid samples or liquid reagents between receptacles, such as between sample containers, reagent containers and reaction cuvettes disposed on the analyzer. Hereinafter, variations of the term aspirate refer to all of such processes for extracting liquid from one container and depositing at least some of the liquid into the same or another container and further includes the supporting devices required to complete the liquid handling operations.

Aspirators typically comprise an elongated, needle-like probe or pipette having a hollow passage whereby liquid may be aspirated into and/or dispensed from the probe using appropriate pumping resources. The pipette may be carried by a transport mechanism adapted to provide horizontal and vertical movement so as to enable the pipette tip to be lowered into a liquid in a reservoir for aspiration of the liquid, and for transporting the liquid to a another location whereat the pipette is lowered to an optimal position for dispensing the liquid. Some type of device, such as a piston assembly, which may be incorporated into the pipette, is operated electronically to aspirate liquid into the pipette and to dispense liquid from the pipette using vacuum pressures.

It is desirable, when aspirating a liquid, to quickly and accurately determine if the amount of liquid available for aspiration is smaller than the desired amount of aspirated liquid; that is, if air is aspirated into the probe during an aspiration process. Various methods are known for detecting such a "short sample" situation as described below.

U.S. Pat. No. 6,938,504 discloses a liquid dosing process in which a temporal course of at least one state variable of a medium is determined essentially over the entire duration of the dosing process and is mathematically compared with a pre-determined state variable nominal range by correlation.

U.S. Pat. No. 6,370,942 discloses a method for determining aspiration of air by employing three separate aspiration tests including a pressure difference test to verify liquid was aspirated. Three algorithms are employed using data acquired throughout the aspiration process and each must produce a positive result for the sample to be released for transfer elsewhere.

U. S. published patent application 20070143063, incorporated herein by reference, discloses and a method for verifying the integrity of an aspiration process by determining the profile of an entire aspiration pressure curve and then determining by numerical analysis whether the difference between the actual and the mathematical is less than the standard deviation of the residuals of a linear regression analysis of an aspiration pressure curve measured on a sample known to have clots therein or known to be less than a desired aspiration volume.

In the short sample detection schemes described above, the shape of the aspiration curve is generally analyzed over a fairly large portion of the full aspiration process. Typically, these systems depend on measuring vacuum pressure at different pre-determined intervals throughout the aspiration process and comparing calculated values to a range of predetermined satisfactory values. However, as the state of the art in clinical analyzers advances, the amount of operational data processed by an analyzer's controller has increased dramatically, placing a premium on the amount of time during which operational situations like a short sample are detected as well as reducing the amount of data required to be reported while monitoring the analyzer's operational status. Hence, there is a need for a more efficient method for determining the insufficiency of sample during a liquid aspiration process, in particular a method that requires less data acquisition than required in the known art.

SUMMARY OF THE INVENTION

It is therefore an object of this invention to provide a method for ascertaining the sufficiency of the amount of liquid which has been aspirated into a pipette tip. This is accomplished by determining the standard deviation of the residuals from a linear regression analysis of the aspiration pressure profile over a shortened final portion of an aspiration pressure curve representative of the aspiration process. It has been discovered that if the standard deviation of the residuals is greater than a predetermined critical value, then the aspiration process has been conducted on a sample having at least the desired liquid volume.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
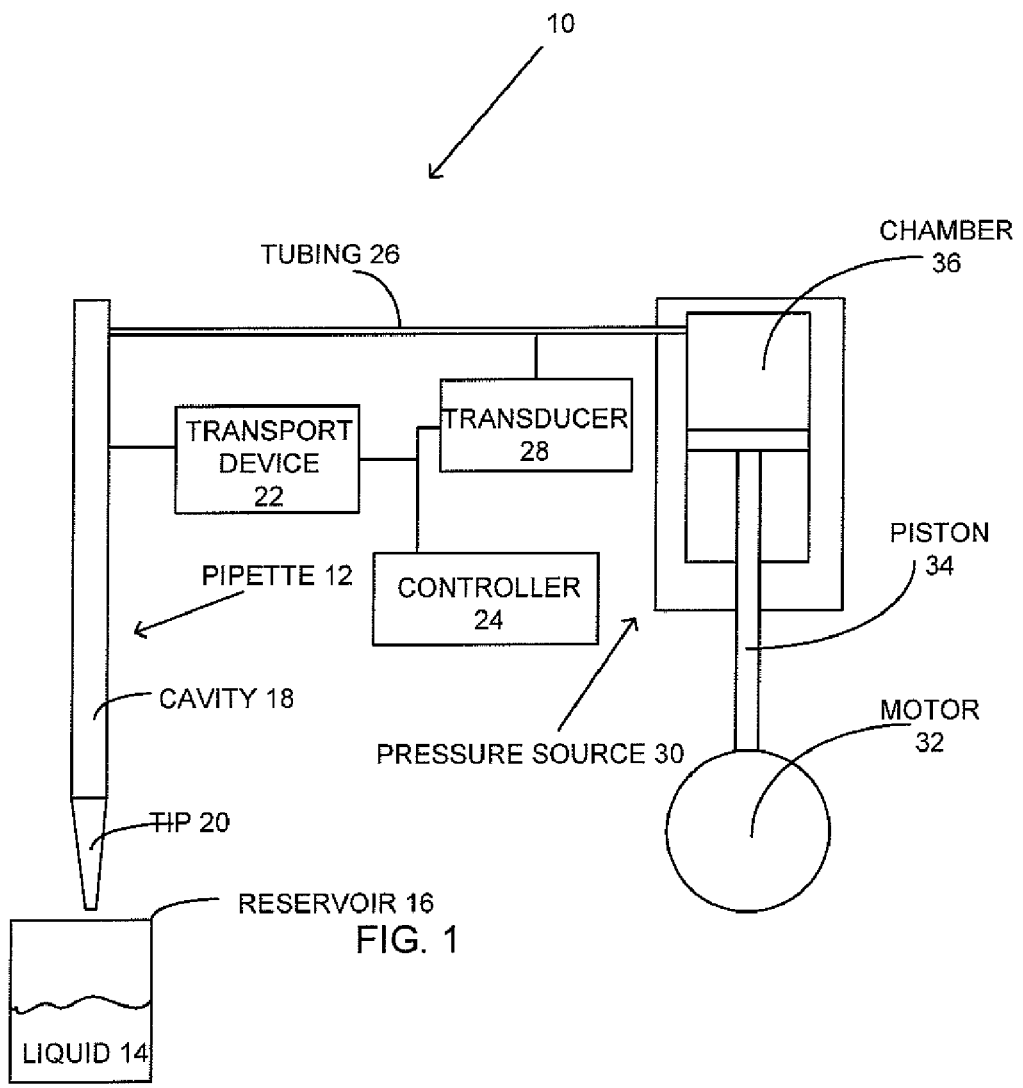
FIG. 1 is a schematic representation of an aspiration system in which the present invention may be practiced.

FIG. 1 illustrates a conventional liquid aspiration system 10 useful in practicing the present invention which includes a pipette 12 for aspirating and dispensing liquid such as a sample liquid 14 stored in a reservoir 16, like described in co-pending U.S. patent application Ser. No. 11/857,922 (DCS-9248) assigned to the assignee of the present application and incorporated herein by reference. Although one such sample liquid 14 is shown for the purpose of describing the liquid dispensing system 10, it will be apparent to those skilled in the art that any number of sample liquid reservoirs can be present in an automated clinical analyzer like described in co-pending U.S. patent application Ser. No. 11/941,204 (DCS-9238) assigned to the assignee of the present application and incorporated herein by reference, including patents and patent applications incorporated therein by reference and like described in co-pending U.S. patent application Ser. No. 10/862,507 (DCS-9159) assigned to the assignee of the present application and incorporated herein by reference, including patents and patent applications incorporated therein by reference. In an exemplary embodiment, the liquid aspiration system 10 may be used in an automated clinical analyzer (not shown). Such automated clinical analyzers are well known in the art and those skilled in the art will know with certainty the functions of the elements of the analyzers to which reference is made.

Pipette 12 generally includes a central cavity 18 which may be adapted to carry a replaceable pipette tip 20 which may have a conically narrowing nose shape terminating in a distal orifice 40 through which liquid is aspirated into cavity 18, and through which liquid is dispensed therefrom. Central cavity 18 opens into the tip cavity upon engagement of the holder with the tip. Alternately, pipette tip 20 may be integral with central cavity 18. Aspiration system 10 further comprises an aspiration/dispensing pressure control 30 adapted to produce a vacuum pressure within cavity 18 during aspiration and a positive pressure during dispensing. Pressure source 30 is connected to pipette by tubing 26 and the pressure therein is monitored with a conventional pressure transducer 28 interfaced to a system computer-based controller 24 programmed to practice the present invention as well as to control the operation of an analytical analyzer associated therewith. Typical of pressure source 30 is a piston assembly 32 connected with tubing 26 and the pipette 12 on a top side thereof, opposite pipette tip 20. Aspiration systems 10 like seen in FIG. 1 are well known to those skilled in the art and may be concocted with a variety of components and designs. Practicing the present invention requires only that pressure be used to cause liquid aspiration and dispensing from pipette 12 and that the aspiration pressure be monitored.

Liquid aspiration system 10 typically includes a transport device 22, indicated diagrammatically, which may be of any suitable type. The transport device 22 is capable of moving the pipette 12 laterally (the X-direction), vertically (the Z-direction) and from front to back (the Y-direction) in an analyzer to enable the pipette 12 to pick up a pipette tip 20 (when disposable tips are used), aspirate liquid 14 into the pipette tip 20 from a sample liquid reservoir 16 or tube 16 and to dispense a desired amount of sample liquid into a test assay element or other container (not shown). Generally, steppermotors, electronic drivers, interface circuits and limit-switches are used within transport device 22 to control transporting the pipette 12 and these are interfaced to system computer 24. Alternately, pipette 12 may be translated along the vertical z-axis by a rack-and-pinion drive. Conventional electronics are used to interface the transport device to the computer 24.

As shown, pipette 12 has a cavity 18 for holding liquid 14 and a tube 26 connected therefrom to a vacuum pressure measurement device or transducer 28 and to pressure control 30 for producing a variable vacuum pressure throughout the pipette 12 responsive to commands from computer 24. Such devices and sources are well known in the art. Commercially available pipettes 12 made from metals like stainless steel or plastics like polypropylene and similar materials, and tubing 26 made from vinyl, polypropylene, polyethylene, metal, etc, may used in the present invention. Pressure measurement device 28 measures air pressure within the pipette 12 both continuously and periodically during the aspiration method of the present invention. An exemplary pressure measurement device 28 is a pressure transducer (Model SCXL004DN from SenSym, Miltipas, Calif.) and it is interfaced to the computer 24 to provide a measured air pressure within tubing 26 to computer 24.

An exemplary aspiration pressure control 30 is a piston-syringe device, mechanically connected to a stepper motor 34 and encoders or home limit-switches (not shown) capable of controlling the movement of the syringe piston and causing pressure control 30 to aspirate and dispense air through tubing 26. Aspiration pressure control 30 and pressure sense device 28 are electronically interfaced to computer 24 which is used to control the operation of the liquid aspiration system 10. The computer 24 also provides signals to control the movement of the pipette 12 via transport device 22 as well as the aspiration into, and dispensing of liquid from, the pipette tip 24.

In such an instance, as illustrated in FIG. 1, pressure control 30 comprises a piston 34 attached to motor 32 for advancing and retracting the piston 34 within a closed chamber 36. A downward movement of piston 34 tends to increase the volume of the chamber 36, thereby to create vacuum or negative air pressure within the chamber 36 which draws air from the interconnected tubing 26, cavity 18, and pipette tip 20 into cavity 18 for aspirating liquid 14 into pipette tip 20. Advancing piston 34 into chamber 36 decreases the volume of chamber 36, thereby to provide a positive air pressure which pushes air out of chamber 36 into the interconnected tubing 26, cavity 18, and pipette tip 20 for expelling and dispensing liquid from the pipette tip 20 via the tip orifice. Thus, the piston 36 provides for aspiration of liquid into, and dispensing of liquid from, the pipette tip 20.

In accordance with the present invention, aspiration pressure control 30 and pressure sense device 28 are controlled and analyzed by computer 24 so as to determine the sufficiency of volume of the aspirated sample liquid 14 through analysis of a pressure profile generated during an abbreviated portion of the full aspiration process. By determining the sufficiency of the aspirated sample liquid 14 over only an abbreviated portion of the full aspiration cycle, the present invention reduces the time required to report pressure data to the analyzer's controller as well as the amount of data required to make such a determination.

A key feature of the present invention is analyzing pressure measurements from pressure transducer 28 to ascertain so-called "short sample" only during a shortened final portion of an aspiration process without requiring pressure measurements during the remainder of the process. Aspiration pressure transducer 28 is activated only for a specified number pressure measurement reads from pressure transducer 28 prior to the end of pumping action or sample aspiration. Pressure data, for instance using an A/D (analog signals converted to digital data) converter, are collected for a period long enough to capture only a final portion the entire aspiration process. The pressure data are collected in real time during the aspiration cycle. In a typical embodiment, an analog input subsystem reads the pressure sense device at a constant rate (for example, 500 Hz) time stamping each reading and buffering the reading(s) for eventual inclusion into the aspiration data set. In parallel to the aspiration process, the pressure data are periodically transferred from the analog sub-system buffer into the aspiration data set. The aspiration data set consists of a series of time stamped pressure readings that occur before and during the initial portion of pump operation. Each process event (start of aspiration cycle, start of pump cycle, end of aspiration pressure readings) is marked in the data set. To achieve close coupling with process event, the data are also read from the analog sub-system coincident with these events. The resultant aspiration data set then contains a multiple of time stamped pressure and event markers that allow analysis of the relevant portion of aspiration process.

Sensing of the upper surface portion of the sample liquid 14 may be performed via system 10 using capacitive level sensing techniques known in the art and like that described in U.S. Pat. No. 7,150,190, assigned to the assignee of the present application and incorporated herein by reference. The technique disclosed therein confirms that a change in capacitance within a liquid level sensor is caused only by true physical contact between a probe and a liquid by verifying that any change in capacitance of the liquid level sensor is repeatable and constant over a given time period and thereby is caused by actual contact the probe and liquid and is not caused by spurious electrical disturbances or other measuring irregularities.

Once liquid level in the reservoir 16 has been determined, sample aspiration commences. A vacuum generated by the aspiration pressure control 30 draws sample liquid 14 up into the pipette tip 20. At the sample time, pipette 12 descends to follow the level of the sample down in reservoir 16, keeping the tip 20 immersed in liquid 14. Different descent rates are used, depending on the diameter of the reservoir 16. After aspiration is completed, the pressure profile recorded only during a near-final portion of the event is examined as described hereinafter and pipette tip 20 is retracted from liquid sample 14. Finally, a quantity of air may be aspirated into tip 20 to move aspirated sample liquid 14 away from the bottom of tip 20 to prevent potential drips.

The rate of aspiration is chosen to provide a pressure profile with the features necessary for aspiration success analysis described below while minimizing cycle time and keeping the magnitude of the pressure signal within the limits of the pressure transducer 28.

Figure 2:
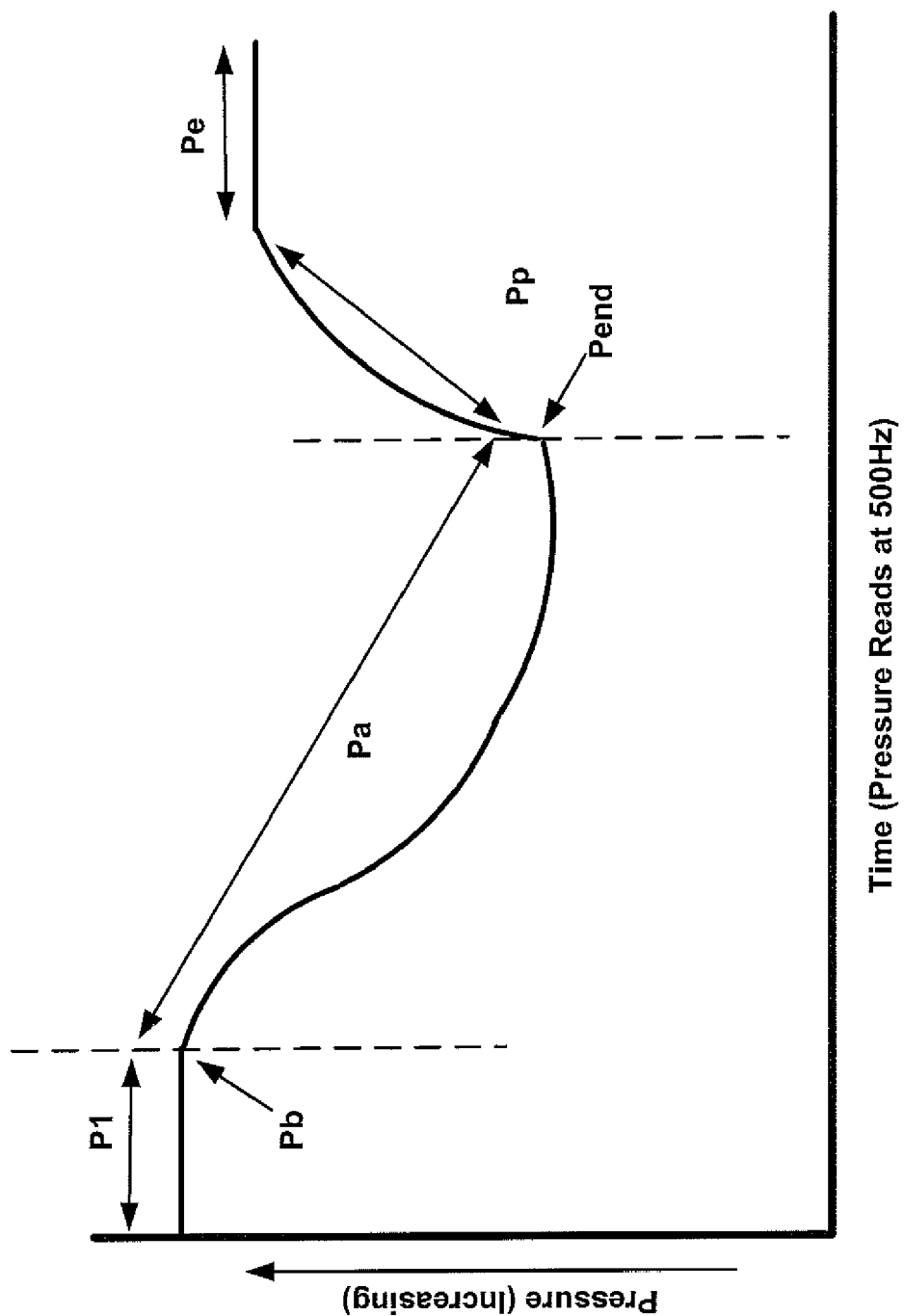
FIG. 2 is a graphical representation of a typical aspiration pressure profile obtainable with the aspiration system of FIG. 1 illustrating sample of sufficient volume to enable a successful sample aspiration.

FIG. 2 is illustrative of the well-known aspiration pressure profile is a graphical representation of a typical aspiration pressure profile obtainable with the aspiration system of FIG. 1 illustrating sample of sufficient volume to enable a successful sample aspiration. The aspiration process of FIG. 2 includes the following events:

P1=averaged relative pressure prior to actual aspiration of liquid into pipette 20

Pb=relative pressure at beginning of actual aspiration of liquid into pipette 20

Pa=pressure measurement range during actual aspiration

Pend=pressure at end of actual aspiration of liquid into pipette 20

Pp=pressure prior to equilibrium after aspiration

Peq=relative pressure at equilibrium after aspiration

One of the parameters known to affecting an aspiration process is the desired volume of aspirated liquid 14. Computer 24 is programmed, among other operations, to control the operation of the liquid aspiration system 10 to deliver such a desired volume, in particular by operating aspiration pressure control 30 for a predetermined length of time after Pb is established This is the period of time, the "aspiration cycle time" during which pressure measurements are made during aspiration, ending at a point in time at which Pend, pressure at end of aspiration, is achieved.

Figure 3:
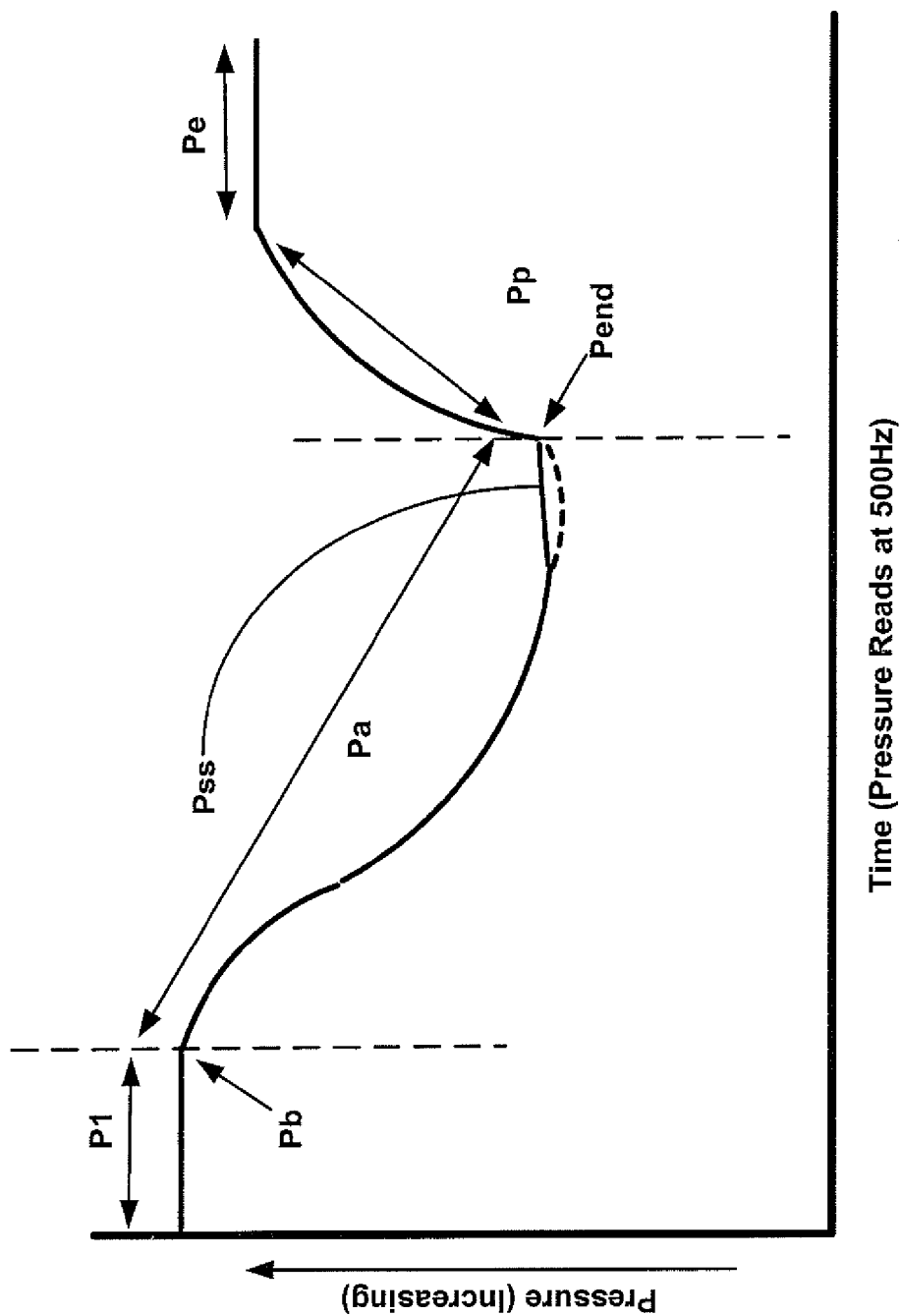
FIG. 3 is a graphical representation of an aspiration pressure profile obtainable with the aspiration system of FIG. 1 illustrating sample of insufficient volume to enable a successful sample aspiration in accord with the present invention.

The present invention monitors the aspiration process for the aspiration of air due to a sample being short over a limited portion of the aspiration cycle covering a period of time immediately prior to Pend. FIG. 3 is a graphical representation of an aspiration pressure profile obtainable with the aspiration system of FIG. 1 illustrating sample of insufficient volume to enable a successful sample aspiration in accord with the present invention. The invention is based on the fact that, during the Pend range, if a short sample is encountered, the pressure measured by pressure transducer 28 will level off as indicated by the generally horizontal line identified as "Pss" in FIG. 3. In order to reduce analyzer system load on computer 15, the Pend range is generally selected to be in the range of about 20% of the full aspiration cycle that begins with Pb and ends at Pend. The dashed line in FIG. 3 is indicative of a proper aspiration process and is included to contrast the overall shape of a proper and a short-ample aspiration processes.

An aspiration is unsuccessful when the pressure-time profile during aspiration does not match that the desired pressure profile obtained for a liquid in the absence of abnormalities or non-uniformities. The degree of match may be obtained using any of a number of well-known numerical analysis techniques which approximate actual computations of an integral representing the difference between the measured pressure profile and the pressure profile in the absence of abnormalities or non-uniformities. As is known, every definition of an integral is based on a particular measure: the Lebesgue integral is based on Lebesgue measure and the Riemann integral is based on Jordan measure. The study of measures and their application to integration is known as measure theory. In general, these techniques are some form or another of a Lebesgue integral which is defined in terms of upper and lower bounds of the functions to be compared using the Lebesgue measure of a set. It uses a Lebesgue sum of the Lebesgue measures of the set of points for which values are approximated. This type of integral covers a wider class of functions than does the Riemann integral, the integral popularly encountered in calculus texts and used by physicists and engineers. Newton-Cotes formulas are another straightforward family of numerical integration techniques. To integrate a function over some interval, it is divided into equal parts and polynomials which approximate the tabulated function are determined and integrated to approximate the area under the curve. Lagrange interpolating polynomials are used to find the fitting polynomials. The resulting formulas are called Newton-Cotes formulas, or quadrature formulas. If the function is given explicitly instead of simply being tabulated at the values, the best numerical method of integration is called Gaussian quadrature. By picking the intervals at which to sample the aspiration pressure, this procedure produces more accurate approximations of the variance between actual and desired pressure profiles (but is more complicated to implement).

Alternately, Simpson's rule, a Newton-Cotes formula, can be used to approximate the integral of variance between actual and desired pressure profile by using quadratic polynomials (i.e., parabolic arcs instead of the straight line segments used in the trapezoidal rule). Simpson's rule can be derived by integrating a third-order Lagrange interpolating polynomial fit to the function at three equally spaced points. Since it uses quadratic polynomials to approximate functions, Simpson's rule actually gives exact results when approximating integrals of polynomials up to cubic degree.

A Gaussian quadrature can be alternately employed to obtain the best numerical estimate of the pressure variance by picking optimal abscissas at which to evaluate the function. The fundamental theorem of Gaussian quadrature states that the optimal abscissas of the m-point Gaussian quadrature formulas are precisely the roots of the orthogonal polynomial for the same interval and weighting function. Slightly less optimal fits may be obtained from Radau quadrature or Laguerre quadratures. Techniques such as these may be employed to advantage in performing the present invention, however, because the degree of accuracy in determining the extent to which the measured pressure-time profile during aspiration does not match the pressure-time profile known to be achieved for a liquid in the absence of abnormalities or non-uniformities is but a relative measure, a less sophisticated numerical analytical technique, known as standard deviation of the residuals is employed in the present invention.

The difference between the measured profile and the expected profile is at a particular time the residual at that time. The standard deviation of the residuals over the time of a profile measures the fit or lack of fit between a profile in the absence of abnormalities or non-uniformities and the measured profile. However, low standard deviation of the residuals is not by itself an indicator of a successful sample volume aspiration.

The residuals can consist of both random error and systematic error parts referred to as the variance error and the bias error. (N. R. Draper and H. Smith, "Applied Regression Analysis," John Wiley & Sons, 1966, pp. 36 . . . ) For the present invention either error indicates an abnormality or non-uniformity of the aspirated liquid. A high standard deviation of the residuals would suggest that the sample was abnormal or had non-uniformities. There are a number of other well-known mathematical procedures for testing that the standard deviation of the residuals does or does not exceed a given value. (Abraham Wald, "Sequential Analysis," Dover Publications, 1947, pp. 125)

Figure 4:
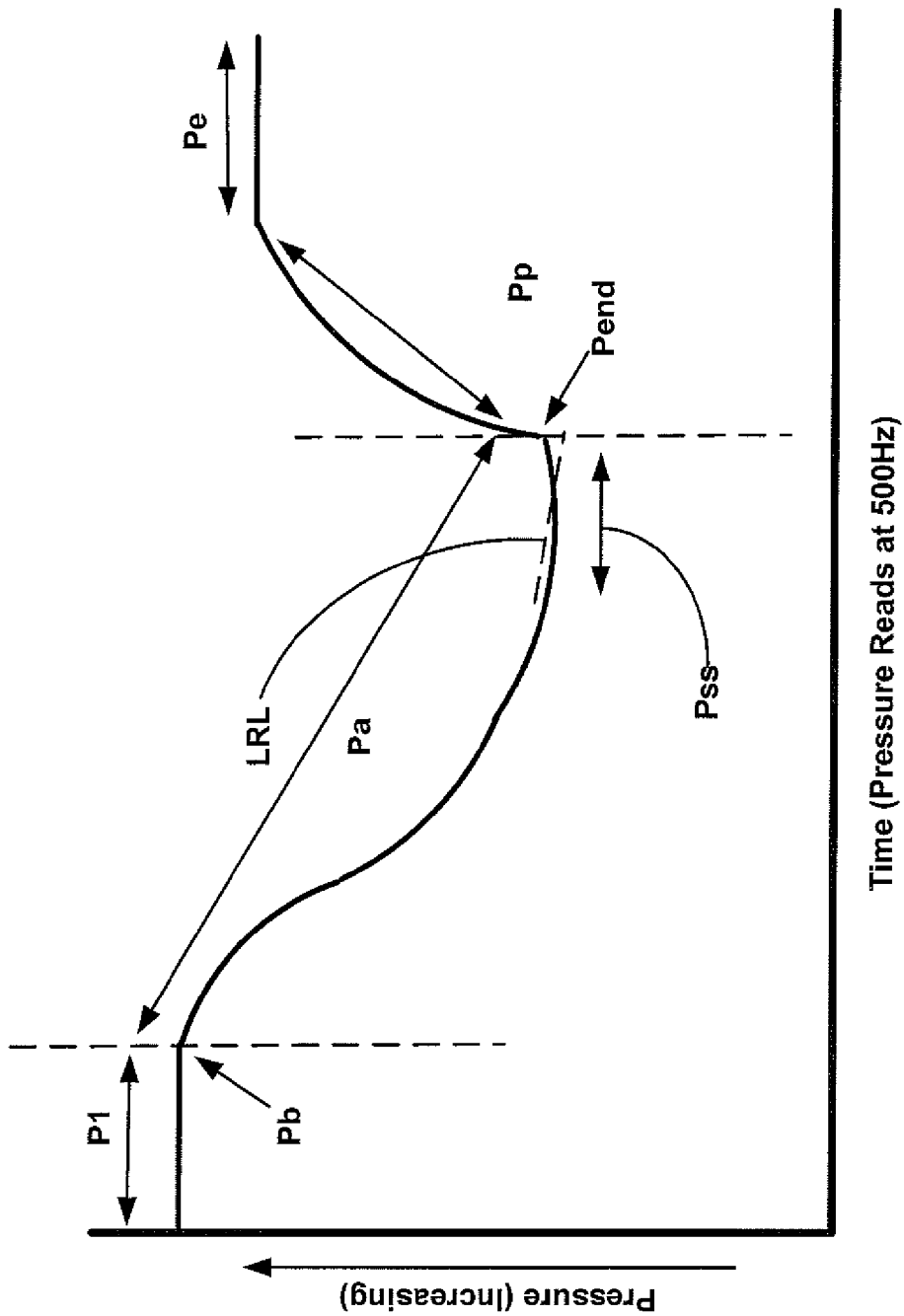
FIG. 4 is a graphical representation of a linear regression analysis of pressure data obtained during a relatively brief portion of a "normal" aspiration pressure profile obtained from a sufficiently large sample volume; and, FIG. 5 is a graphical representation of a linear regression analysis of pressure data obtained during a relatively brief portion of a "normal" aspiration pressure profile obtained from a insufficiently large sample volume, in accord with the present invention.

To ascertain the presence of short-sample during aspiration, in accordance with the present invention, pressure data are obtained by pressure transducer 28 during a relatively brief portion Tss in the range of about 20% of a "normal" aspiration pressure profile obtained from a sufficiently large sample like shown in FIG. 4. Using these pressure data, a linear regression analysis is conducted in order to determine the slope b and intercept a of the general regression equation when written as Y=a+b X, in this case, Y=pressure and x=time of aspiration. The results of such a calculation is seen in FIG. 4 as dashed "Linear Regression Line" LRL. Next, the variation between the actual and theoretical pressure data is mathematically determined using any of a number of numerical techniques like those discussed above.

In an exemplary embodiment, the residual variance is calculated as a measure of the variation of the actual pressure values about the linear regression line LRL. Residual Variance RV is given by the following equation where y is the actual measured pressure value, y' is the pressure calculated by the LRL formula, y-y' is the residual, and n is the number of data points.

$$(RV)^2 = (y-y')2\ n-2$$

The square root of the Residual Variation is the standard deviation of the estimated residuals. It has been discovered that if the standard deviation of the residuals (y-y') is greater than a predetermined value, then there was insufficient sample to aspirate the desired volume. This predetermined value may be experimentally determined by aspirating a liquid sample having less than a desired volume of liquid and calculating the standard deviation of the residuals for such an improper aspiration.

Figure 5:
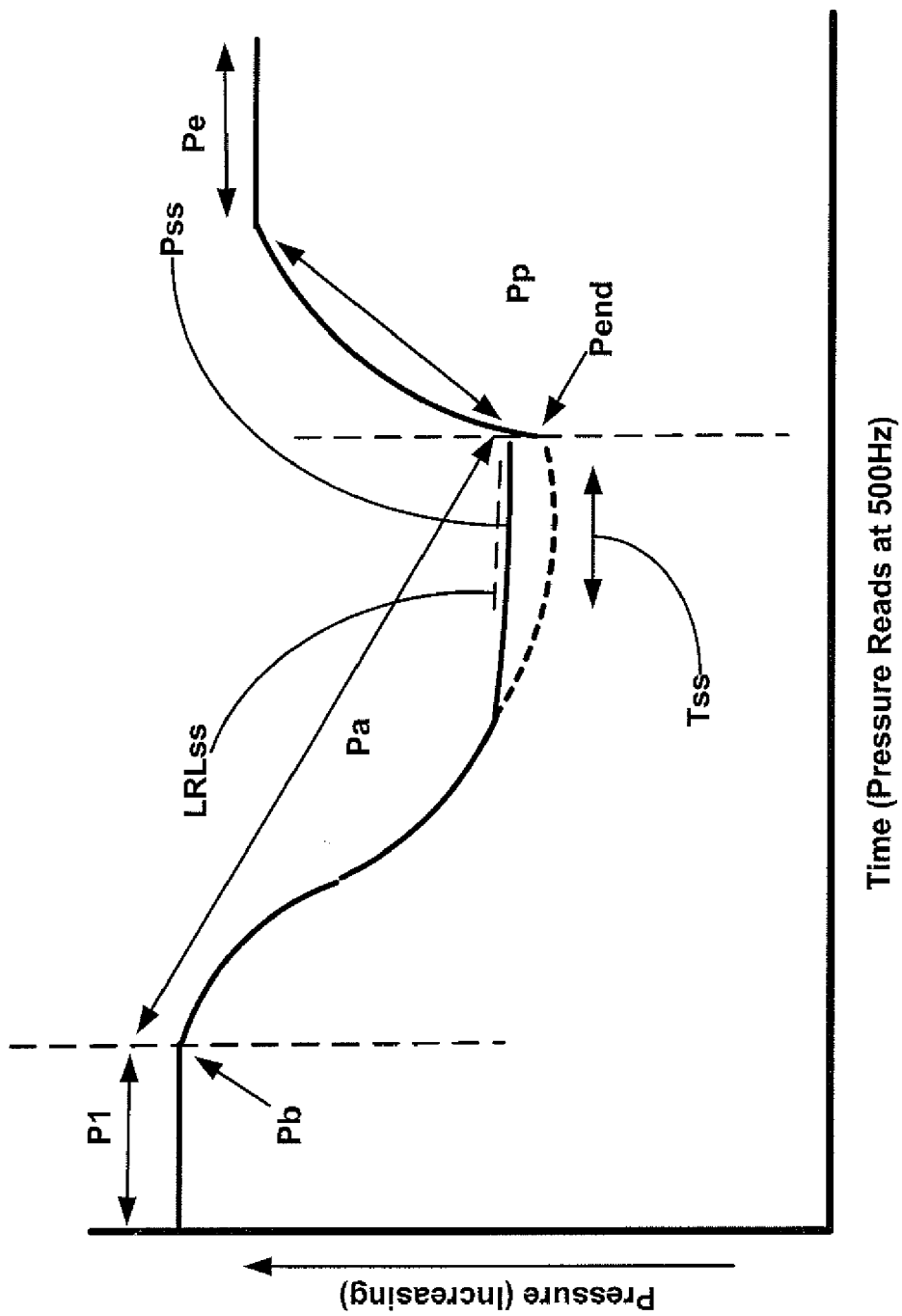

FIG. 5 is a graphical representation of an aspiration pressure profile obtainable with the aspiration system of FIG. 1 illustrating a linear regression analysis of an aspiration pressure curve obtained in accord with the present invention in the instance of a short-sample. A comparison of the standard deviation of the residuals for the LRL of the sufficient volume sample aspiration profile of FIG. 4 and of the standard deviation of the residuals for the LRLss for the insufficient volume sample aspiration profile of FIG. 5 over only the shortened final portion of the aspiration cycle covering a period of time Tss immediately prior to Pend shows that the residuals of the LRL of a sufficient volume sample aspiration profile will be larger than the residuals of the LRLss of a short-sample having insufficient volume sample aspiration pressure profile. With minimal experimentation, for example by comparing the residuals of the LRL of a sufficient 250 uL volume sample aspiration profile with the residuals of the LRL of an insufficient 200 uL and 150 uL volume sample aspiration profile, it is possible to determine a critical value that the LRL of an insufficient volume sample aspiration will be less than. This critical value is affected by a number of variations in the design of aspiration system 10, (for example, variations in central cavity 18, pipette tip 20, pressure source 30, tubing 26, pressure transducer 28 and the like), it is not possible to determine a universally applicable "critical value" of residual values thus requiring such a calibration process to determine the range of residual standard deviations associated with "sufficient volume aspiration profiles". The present invention thus provides an improved method for ascertaining or confirming that an aspiration process has been conducted for a sample 14 that is of sufficient sample volume without requiring that pressure values be evaluated for the entire aspiration process as is routine in the prior art.

Those skilled in the art will appreciate that the embodiments of the invention disclosed herein are illustrative of the principles of the invention and that other modifications may be employed which are still within the scope of the invention. For example, the variance of the measured pressure-time profile during aspiration from that of a profile in the absence of abnormalities or non-uniformities may be obtained to a higher degree of accuracy using more sophisticated numerical integration techniques, like Newton-Cotes formulas, Simpson's rule or Gaussian quadrature. Obvious variants of the invention should also be applicable to a fluid-coupled system with a few adjustments to the parameters. Accordingly, the present invention is not limited to those embodiments precisely shown and described in the specification but only by the following claims.

The invention claimed is:

1. A method for determining that a liquid sample volume aspirated in an aspiration process is at least as large as a desired volume by:

determining the profile only during a shortened final portion of an aspiration pressure curve representative of said aspiration process without requiring pressure measurements during the remainder of the aspiration process;

calculating a first integral representation of the shortened final portion of the aspiration pressure curve;

calculating a second integral representation of the shortened final portion of the aspiration pressure curve of a sample known to be of sufficient volume;

determining if the standard deviation of the residuals of the difference between the profile of the shortened final portion and the first integral representation of the shortened final portion is at least as great as the standard deviation of the residuals of the difference between the profile of the shortened final portion and the second integral representation, and, confirming thereby that the aspirated liquid sample volume is at least as large as the desired volume.

2. The method of claim 1 wherein said shortened final portion of the aspiration pressure curve is the portion immediately prior to the end of aspiration.

3. The method of claim 2 wherein said shortened final portion of the aspiration pressure curve is on the order of about 20% of the full aspiration process.

4. The method of claim 1 wherein said first integral representation is a zero slope linear mathematical representation and wherein said second integral representation is also a zero slope linear mathematical representation.

5. A method for determining that a liquid sample aspirated in an aspiration process has a smaller volume than a desired volume by:

determining the profile only during a shortened final portion of an aspiration pressure curve representative of said aspiration process without requiring pressure measurements during the remainder of the aspiration process;

calculating a first integral representation of the shortened final portion of the aspiration pressure curve;

calculating a second integral representation of the shortened final portion of the aspiration pressure curve of a sample known to be of sufficient volume;

determining if the standard deviation of the residuals of the difference between the profile of the shortened final portion and the first integral representation is less that the standard deviation of the difference between the profile of said shortened final portion and the second integral representation, and, concluding thereby that the aspirated liquid sample has less than the desired volume.

6. The method of claim 5 wherein the shortened final portion of an aspiration pressure curve is the portion immediately prior to the end of aspiration.

7. The method of claim 6 wherein the shortened final portion of an aspiration pressure curve is on the order of about 20% of the full aspiration process.

8. The method of claim 5 wherein said first integral representation is a zero slope linear mathematical representation and wherein said second integral representation is also a zero slope linear mathematical representation.

* * * * *